United States Patent [19]

Scott et al.

[11] Patent Number: 4,727,088

[45] Date of Patent: Feb. 23, 1988

[54] RETINOID COMPOSITION HAVING ENHANCED BIOAVAILABILITY AND PERCUTANEOUS ABSORPTION

[75] Inventors: Richard A. Scott, Burbank; Mitchell S. Wortzman, Los Angeles, both of Calif.; Eric Jungermann, Phoenix, Ariz.

[73] Assignee: Neutrogena Corporation, Los Angeles, Calif.

[21] Appl. No.: 941,698

[22] Filed: Dec. 15, 1986

Related U.S. Application Data

[63] Continuation-in-part of Ser. No. 577,513, Feb. 6, 1984, Pat. No. 4,678,663.

[51] Int. Cl.$^4$ .......................... A61K 7/48; A61K 31/20
[52] U.S. Cl. .......................... 514/725; 424/DIG. 5; 514/859; 514/863
[58] Field of Search ............................. 514/725, 859

[56] References Cited

U.S. PATENT DOCUMENTS 4,022,913  5/1977  Newmark .......................... 514/725
4,603,146  7/1986  Kligman .......................... 514/725

Primary Examiner—Dale R. Ore
Attorney, Agent, or Firm—Richard R. Mybeck

[57] ABSTRACT

A new and improved topically applied pharmaceutical preparation for the treatment of acne and an improved vehicle for delivering the active ingredients thereof to the human skin in a manner whereby the bioavailability and percutaneous absorption of the active ingredient is remarkably enhanced. The vehicle comprises a volatile silicone, a fatty alcohol having from 12–22 carbon atoms, retinoids selected from the group consisting of tretinoin (all-trans retinoic acid) and isotretinoin (13-cis retinoic acid); and such preservatives or emulsifying agents as may be warranted.

11 Claims, No Drawings

RETINOID COMPOSITION HAVING ENHANCED BIOAVAILABILITY AND PERCUTANEOUS ABSORPTION

This application is a continuation-in-part application from U.S. Ser. No. 577,513, filed Feb. 6, 1984, now U.S. Pat. No. 4,678,663.

INTRODUCTION

This invention relates to topical pharmaceutical preparations for the treatment of acne and more particularly to a new and improved topically applied pharmaceutical product and means for delivering the same in a manner whereby the bioavailability and effectiveness of the active ingredient thereof is remarkably enhanced.

BACKGROUND

The prior art has traditionally delivered topically effective pharmaceutical agents in creams, lotions and gels, all of which require the user to soil his fingers and hands in the application of such medicaments and in the subsequent action of "rubbing it in". Further, such products are greasy, slow to dry and inevitably leave a residue which not only is visible, but rubs off onto clothing and the like, all of which are discomforting to the social ease of the user.

One variation from the traditional creams, lotions and gels occurred with the development of the so-called stick delivery systems which were used to apply antiperspirants, deodorants, lip balm, lip coloring and like ingredients which are generally applied to the surface of the skin.

Antiperspirant sticks based on the combination of a volatile silicone, a fatty alcohol and a powdered antiperspirant were recently developed and marketed. These sticks, however, have not been extended beyond simple antiperspirant sticks using water soluble inorganic antiperspirant salts. This limited use is the result of the known mechanism of antiperspirant vehicles and the need to intentionally design such delivery systems so as to limit the amount of active ingredient (antiperspirant) which can penetrate into the skin. For an antiperspirant to be efficacious, a large concentraion of the active ingredient must be maintained on the surface of the skin from whence it is slowly dissolved and diffused into the aprocrine ducts, rather than being absorbed through the skin. To extend this prior art to other pharmacologically active topical agents, it is necessary to greatly enhance the amount of the drug which is able to penetrate through the skin to reach the desired sites of action. This absorption of a drug through the skin is referred to as percutaneous absorption.

Nor does the typical lip balm formulation solve the problem because such products normally contain large amounts of wax (such as Beeswax, Carnauba, and the like), and oils, (such as, castor oil, lanolin and the like), whereupon a greasy/oily sensation is created on the skin which is not only unpleasant but gives the user the feeling of being "dirty". In addition, this type of formulation, as with antiperspirants, severely limits the percutaneous absorption of most drugs through the skin.

Likewise, the conventional creams and lotions fail to obviate the problems enumerated because the creams and lotions are excessively greasy and have the potential to sequester the active ingredient so that the percutaneous absorption of the drug and its efficacy is reduced.

SUMMARY OF INVENTION

An improved topically applied pharmaceutical preparation for treating acne including a novel delivery system by which the bioavailability and percutaneous absorption of the active pharmaceutical ingredient is remarkably enhanced, the "feel" of the product is pleasing to the user, it is simple and neat to use, and its compatibility enables retinoids selected from the group consisting of tretinoin (all-trans retinoic acid) and isotretinoin (13-cis retinoic acid) to be incorporated thereinto without any material depreciation of the unique properties accorded thereto.

Accordingly, one object of the present invention is to develop a consumer acceptable delivery system for applying an active pharmaceutical to the human skin which avoids the aforesaid disadvantages of the prior art creams, lotions, gels and sticks while enabling the user to readily control its application to a specified location with maximum effectiveness, a minimum of waste, and no mess.

Another object of the present invention is to provide a silky and non-greasy delivery system which is capable of spreading an active pharmaceutical ingredient evenly and smoothly on the skin and which leaves virtually no residue.

A further object of the present invention is to provide a new and improved delivery system which is compatible with dermatologically effective pharmaceuticals and is capable of delivering such pharmaceuticals with high efficiency and increased percutaneous absorption thereby increasing both the bioavailability of the active ingredient and its efficacy.

Still another object of the present invention is to provide an improved topically applicable pharmaceutical preparation which can be used to efficiently and efficaciously treat acne.

These and still further objects as shall hereinafter appear are fulfilled by the present invention in a remarkably unexpected fashion as will be readily discerned from a careful consideration of the detailed description of certain exemplary embodiments thereof which hereafter appear.

DETAILED DESCRIPTION OF PREFERRED EMBODIMENTS

The present invention relates to a pharmaceutical preparation and more particularly to a semi-solid vehicle containing retinoids selected from the group consisting of tretinoin (all-trans retinoic acid) and isotretinoin (13-cis retinoic acid) for applying that to the human skin for the treatment of acne. The special vehicle comprises a volatile silicone, such as dimethicone and cyclomethicone; a fatty alcohol having from 12 to 22 carbon molecules or a mixture of $C_{12}$ to $C_{22}$ fatty alcohols; retinoids selected from the group consisting of tretinoin (all-trans retinoic acid) and isotretinoin (13-cis retinoic acid); and such preservatives, or emulsifying agents as may be warranted.

An important factor of the present invention is the use of a volatile silicone such as dimethicone, the cyclomethicones or equivalent cyclic silicones, which avoid the heavy oils and waxes heretofore employed and provide instead a silky and non-greasy lubricant which enables the active ingredient to be spread evenly and smoothly upon the skin. Once the active ingredient has been delivered to the selected site, the silicones will volatilize and leave no residue on the skin. Suitable silicones for use herein are available commercially from Dow Corning as 200 fluid (0.65 cs), 344 fluid (formerly Q2-1053) and 345 fluid (formerly F1-3597).

The use of Dodecanol, Tridecanol, Tetradecanol, Pentadecanol, Hexadecanol (cetyl alcohol), Heptadecanol Octadecanol, Nonadecanol, Eicosanol, Heneiconsanol, and Docosanol (Stearyl alcohol) or mixtures thereof provide another important feature of the invention.

Specifically the basic delivery system of the present invention contains from about 20% up to about 40% (w/w) of fatty alcohol such as a mixture of stearyl and cetyl alcohol; from about 30% up to about 60% (w/w) volatile silicone such as dimethicone or a cyclomethicone; from about 0.1% up to about 10% (w/w) of the active drug; and from about 1% to about 10% (w/w) of various other ingredients such as preservatives, and/or emulsifying agents.

The system thus described has the further surprising advantage in that it is not limited just to water soluble ingredients but can also be employed in a most propitious manner with many insoluble ingredients when suspended in a fine particulate form (less than about 30 m) to form an acceptable product.

The specific details whereby our system is employed with retinoids selected from the group consisting of tretinoin (all-trans retinoic acid) and isotretinoin (13-cis retinoic acid) for the treatment of acne shall now be described. Special attention is directed to the ability of this system to stabilize a number of drug ingredients which are known to be unstable in most common vehicles, and to accept those active ingredients which heretofore have not been acceptable in any effective vehicle systems.

13-cis retinoic acid (isotretinoin) when effectively incorporated into the present delivery system exhibits improved stability, and enhanced bioavailability as hereinafter demonstrated. The accepted use and the expected shelf-life, as determined by accelerated stability studies, for the 13-cis retinoic acid stick are reported in Table I along with a number of other active pharmaceutical agents which have been found useful when used therewith.

TABLE I

| INGREDIENT | USE | EXPECTED SHELF-LIFE* |
|---|---|---|
| Hydroquinone 2% | Skin Bleaching | 24–36 months |
| Benzoyl Peroxide 5% | Acne Treatment | 24 months |
| Coal Tar Extract 2% | Psoriasis Treatment | 36 + months |
| Allantoin .5% | Dry Skin Product | 24–36 months |
| Glycerin 5% | Dry Skin Product | 36 + months |
| Camomile Extract 1% | Anti-itch Product | 18 months |
| Butaben Picrate 1% | Burn Anesthetic | 18–24 months |
| Hydrocortisone .5% | General Steroid | 24–36 months |
| Providone-Iodine 1% | Antiseptic Product | 24–36 months |
| Bactimycin .5% | Antibiotic Product | 24–36 months |
| Diethyltoluamide 1% | Insect Repellent | 24–36 months |
| Papain | Psoriasis Treatment | 24–30 months |
| 13-Cis Retinoic Acid .1% | Acne Treatment | 18–24 months |

(*Note: When formulated in accordance with present invention.)

From Table I, it can be readily seen that the volatile silicone based vehicle system of the present invention provides an excellent matrix for the stabilization of 13-cis retinoic acid.

Currently there are two retinoids (vitamin A derivatives) which are approved by the FDA for the treatment of acne. They are tretinoin (all-trans retinoic acid) and isotretinoin (13-cis retinoic acid). Current government approvals recognize tretinoin as a topical treatment for acne and isotretinoin is recognized as a systemic reagent. However, clinicals are currently underway to demonstrate isotretinoin as a topically effective reagent. It should also be observed that the retinoids have also been the object of a number of clinical tests which demonstrate a hopeful potenial in reversing the clinical signs of aging, particularly photoaging (i.e., sun induced) and reducing the incidence of skin cancers.

The silicone/fatty alcohol ($C_{12}$–$C_{22}$) system of the present invention further offers a vehicle of low-irritancy potential. This is important in treating skin disorders or sensitive skin with any drug. Many of the vehicles currently used contain ethyl alcohol, isopropyl alcohol, glycols and other moderately irritating substances. The silicone/fatty alcohol system provides a non-stinging, non-irritating and low allergenic vehicle.

The increased bioavailability of the active pharmaceutical agent delivered in accordance with this disclosure, as compared to the more traditional vehicles such as creams and lotions, is a unique result. It is commonly known, in comparing the efficacies of different antiperspirant vehicles, such as creams, aerosols, roll-ons and sticks, that the determining factor is the level of the active ingredient (antiperspirant). That is, the same percentage of active antiperspirant ingredient will produce the same level of antiperspirant effect; regardless of the vehicle used.

As shown in Table II-A, the present invention will Tretinoin demonstrates a substantially improved drug bioavailability, and therefore efficacy, over the liquid and gel forms of tretinoin currently marketed (Retin-A ®, Ortho) which contain five (5) time (liquid) and two and one-half times (gel) as much Tretinoin. Table II-B demonstrates the bioavailability by percutaneous penetration in present penetration of total available dose for a preparation embodying the present invention and containing 0.05 weight percent isotretinoin. Because there is no currently approved topical product containing 13-cis retinoic acid, there is no basis for comparison but it is believed that the data reported in Table II-A is characteristic of expectation. The results shown in Tables II-A and II-B are believed remarkable when compared to what would be expected by simply utilizing prior antiperspirant.

In one practice of the present invention using stearyl alcohol, all of the desired ingredients with the exception of the volatile silicone are mixed together and the mixture is then heated gently to about 80° C. until all of the ingredients are thoroughly mixed throughout the melted stearyl alcohol (MP=80° C.). The melted solution or suspension is then cooled to 60°–70° C. and the volatile silicone is added to the cooled mixture and stirred thereinto. When the silicone is thoroughly mixed throughout, the resulting mixture is poured into suitable molds or containers and allowed to cool until solidified. A propitious effect of this practice is that the active ingredient maintains its homogeneous dispersion throughout the solidified mass and there is little or no settling therein.

The invention has been successfully practiced to produce the stick compositions reported below which are than capable of delivering the noted active pharmaceutical ingredient to the desired sites in an easy and efficient manner.

The user employs the resulting stick by grasping the container in which the vehicle with its active ingredient has been disposed. The conventional push-up container, that is, a container having a base plate which is upwardly mobile in response to a force applied thereto by the consumer, which in turn forces the vehicle upwardly until an applicator surface is exposed above the upper rim of the container, can be considered to typify the container used herein. The user then manipulates the container in a stroke-wise fashion to paint the desired location with the mixture thereby delivering the active ingredient to the situs where its action is desired or required. This, of course is not intended to limit the use of the present invention to only stick forms, but is presented as an example of one potential use.

To further aid in the understanding of the present invention, and not by way of limitation, the following examples are presented.

EXAMPLE 1

A batch of 13-cis retinoic acid-containing vehicle is prepared to provide a product for the treatment of acne. Note that such a product, to be effective, must be capable of penetrating the sebaceous duct through the follicular opening.

A mixture of 13-cis retinoic acid, Laureth-4, PEG-1000, stearyl alcohol, cetyl alcohol, and preservatives are stirred together and gently heated to 80° C. where it is maintained while all of the ingredients are thoroughly blended throughout the molten mass. The molten solution/suspension is then cooled to a temperature between 60°-70° C. and a volatile silicone (cyclomethicone) is added thereto and blended therein. After the silicone is thoroughly mixed with all of the other ingredients, the mixture is poured into a cylindrical mold or container and cooled further until it is completely solidified.

The resulting product, herein denominated "13-cis retinoic acid stick" has the following analysis (in weight percent):

0.05% 13-cis Retinoic Acid (Isotretinoin)
29.0% Stearyl Alcohol
1.0% Cetyl Alcohol
3.0% Laureth-4
6.0% PEG-1000
61.4% Volatile Silicone

EXAMPLE 2

Sticks prepared according to the procedure of EXAMPLE I having 0.01% tretinoin and 0.05% isotretinoin were tested for bioavailability against the only retinoid-containing topical sold for treating acne, namely, Retin-A ® Liquid (0.05% Tretinoin; Ortho) and Retin-A ® Gel (0.025% Tretinoin; Ortho), using the standard protocol for such tests based on FICK'S Law (see: Franz, T. J., "On the bioavailability of topical formulations . . ." J. Amer. Academy of Dermatology, St. Louis, Vol 9, No 1, pp 63–73 at 68–69). The results are reported in Table II-A and II-B, and expressed as penetration in micrograms over a period of 6 hours.

TABLE II-A

Percutaneous Penetration of Tretinoin in Percent Penetration of Total Available Dose

| Time after Application hours | Example I (0.01% T) | Retin-A Liquid (.05%) | Retin-A Gel (0.025%) |
|---|---|---|---|
| 0.5 | 5.9 | 0.6 | 1.2 |
| 1.0 | 6.5 | 1.0 | 0.9 |
| 2.0 | 6.4 | 0.6 | 1.6 |
| 3.0 | 6.4 | 0.6 | 1.8 |
| 4.0 | 5.1 | 0.6 | 1.8 |
| 5.0 | 6.2 | 1.0 | 1.9 |

TABLE II-A-continued

Percutaneous Penetration of Tretinoin in Percent Penetration of Total Available Dose

| Time after Application hours | Example I (0.01% T) | Retin-A Liquid (.05%) | Retin-A Gel (0.025%) |
|---|---|---|---|
| 6.0 | 6.6 | 1.2 | 1.6 |

TABLE II-B

Percutaneous Penetration of Isotretinoin in Percent Penetration of Total Available Dose

| Time after Application hours | Example I (0.05% I) |
|---|---|
| 0.5 | 0.3 |
| 1.0 | 0.6 |
| 2.0 | 1.0 |
| 3.0 | 1.0 |
| 4.0 | 0.7 |
| 5.0 | 0.8 |
| 6.0 | 1.1 |

From the foregoing it becomes readily apparent that a novel and unique vehicle system has been herein described which delivers the retinoids in a form wherein the bioavailability and percutaneous absorption is remarkably enhanced and with which the physical disadvantages of prior art systems have been obviated. Of course, such modifications, alterations and adaptations as will readily occur to the skilled artisan confronted with this disclosure are intended within the spirit of the present invention which is limited only by the scope of the claims appended hereto.

Accordingly, what is claimed is:

1. A pharmaceutical preparation having enhanced bioavailability and percutaneous absorption comprising a mixture containing from about 20% up to about 40% (w/w) fatty alcohol having 12 to 22 carbon atoms or mixtures thereof; from about 30% up to about 60% (w/w) of a volatile silicone; from about 0.01% up to about 10% (w/w) of retinoids selected from the group consisting of tretinoin (all-trans retinoic acid) and isotretinoin (13-cis retinoic acid); and from about 1% to about 10% (w/w) of an ingredient selected from the group consisting of preservative, an emulsifier or a mixture thereof.

2. A preparation according to claim 1 in which said fatty alcohol comprises a mixture of stearyl and cetyl alcohol.

3. A preparation according to claim 1 in which said volatile silicone is cyclomethicone.

4. A preparation according to claim 1 in which said volatile silicone is dimethicone.

5. A preparation according to claim 3 in which said fatty alcohol comprises a mixture of stearyl and cetyl alcohol.

6. A preparation according to claim 4 in which said fatty alcohol comprises a mixture of stearyl and cetyl alcohol.

7. A pharmaceutical preparation for the treatment of acne consisting from about 0.01% up to about 10% (w/w) of 13-cis retinoic acid as its essential ingredient, said ingredient dispersed throughout a semi-solid vehicle having from about 20% up to about 40% (w/w) stearyl and cetyl alcohol; from about 30% up to about 60% (w/w) of a volatile silicone; and from about 1% to about 10% (w/w) of an ingredient selected from the group consisting of preservative, an emulsifier or a mixture thereof.

8. A pharmaceutical preparation according to claim 7 in which said volatile silicone is cyclomethicone.

9. A pharmaceutical preparation according to claim 7 in which said volatile silicone is dimethicone.

10. A pharmaceutical preparation according to claim 5 in which said retinoid is tretinoin.

11. A pharmaceutical preparation according to claim 6 in which said retinoid is 13-cis retinoic acid.

* * * * *